United States Patent
Owades et al.

(10) Patent No.: US 6,610,275 B1
(45) Date of Patent: Aug. 26, 2003

(54) DEVICE FOR TREATING DRINKING WATER TO MAKE IT HOSTILE TO DENTAL PLAQUE

(76) Inventors: Joseph L. Owades, 3097 Wood Valley Rd., Sonoma, CA (US) 95476; Ruth M. Owades, 3097 Wood Valley Rd., Sonoma, CA (US) 95476

( * ) Notice: Subject to any disclaimer, the term of this patent is extended or adjusted under 35 U.S.C. 154(b) by 40 days.

(21) Appl. No.: 10/074,540

(22) Filed: Feb. 13, 2002

(51) Int. Cl.⁷ .............................. A61K 7/16; A61K 7/24; C02F 1/42; C02F 5/10
(52) U.S. Cl. .................... 424/55; 210/282; 210/686; 252/176; 252/179; 424/57; 426/66
(58) Field of Search ................. 252/176, 179; 424/55, 57; 426/66; 210/686, 282; 206/524.6

(56) References Cited

U.S. PATENT DOCUMENTS

| | | | | |
|---|---|---|---|---|
| 2,781,312 A | * | 2/1957 | Klumb et al. | 210/282 X |
| 3,223,619 A | * | 12/1965 | Calmon et al. | 252/179 X |
| 3,589,999 A | * | 6/1971 | McRae et al. | 210/686 X |
| 4,097,588 A | * | 6/1978 | Levine | 424/57 X |
| 4,198,296 A | * | 4/1980 | Doumas et al. | 210/686 X |
| 4,311,607 A | * | 1/1982 | Kaeser | 252/179 X |
| 4,325,975 A | * | 4/1982 | Lindon et al. | 426/66 |
| 4,895,648 A | | 1/1990 | Hankammer | 210/188 |
| 4,919,918 A | | 4/1990 | Cole et al. | 424/44 |
| 4,969,996 A | | 11/1990 | Hankammer | 210/282 |
| 5,145,664 A | | 9/1992 | Thompson | 424/49 |
| 5,211,973 A | * | 5/1993 | Nohren, Jr. | 210/282 X |
| 5,330,749 A | | 7/1994 | Giacin et al. | 424/49 |
| 5,681,475 A | * | 10/1997 | Lamensdorf et al. | 210/666 |
| 5,873,995 A | | 2/1999 | Huang et al. | 210/87 |
| 5,993,785 A | * | 11/1999 | Johansen et al. | 424/57 X |
| 6,080,419 A | * | 6/2000 | Stookey | 424/55 X |
| 6,485,708 B1 | * | 11/2002 | Winston et al. | 424/57 X |

OTHER PUBLICATIONS

"Introduction to Dental Plaque", http://www.dentistry.leeds.ac.uk/OROFACE/PAGES/micro/micro2.html, Sep. 21, 2001, pp. 1–6.

* cited by examiner

Primary Examiner—Richard D. Lovering
(74) Attorney, Agent, or Firm—Hayes Soloway P.C.

(57) ABSTRACT

A device for treating potable water contains a mixed buffer of a cation exchange resin in the hydrogen ion form and an anion exchange resin, a chelating agent and a sparingly soluble calcium salt, all contained in a porous, flow-through bag.

18 Claims, No Drawings

DEVICE FOR TREATING DRINKING WATER TO MAKE IT HOSTILE TO DENTAL PLAQUE

FIELD OF THE INVENTION

The present invention relates to the field of oral hygiene. In particular, the present invention provides a device for treating drinking water to make it hostile to dental plaque.

BACKGROUND OF THE INVENTION

Dental plaque is a general term for the diverse microbial (predominantly bacterial) community found on teeth surfaces. Normally it is maintained by the host, by reversible hydrogen bonds including van der Waals forces. But irreversible adhesion to tooth surfaces occurs when there is a shift in the composition of the plaque microflora. Acidogenic species, such as Streptococci mutans and lactobacilli, flourish when there is a low pH in the plaque. Such pH's can be below 4.5.

Mouthwashes and oral rinses have been in use for many years for controlling build-up of dental plaque. Most commercially available mouthwashes contain a fairly high percentage—up to thirty percent being typical—of ethyl alcohol. While these alcohol-containing mouthwashes are considered generally safe and effective, the inclusion of alcohol has several disadvantages. High alcohol mouthwashes have been linked in some cases to increased incidents of mouth and throat cancer. Also, alcohol-containing mouthwashes can be a poison hazard to a small child, and a health hazard to persons who cannot tolerate alcohol for health reasons. Alcohol-containing mouthwashes also are inappropriate for persons who may avoid alcohol because of religious convictions. Alcohol in a mouthwash also may irritate protective layers of the mouth and throat, and dry out inflamed tissues.

BRIEF DESCRIPTION OF THE INVENTION

The present invention provides alcohol-free means for controlling build-up of plaque by changing the pH of the mouth so as to buffer the effluent that resides with the dental flora. This is accomplished by an aqueous based swish or drink derived from contacting potable water with a mixed buffer of a cation exchange resin in the hydrogen ion form and an anion exchange resin or resins, a chelating agent and a slightly soluble calcium salt. The hydrogen ion form of the cation exchange resin is in equilibrium with a calcium salt, serving to buffer the milieu in the mouth.

DETAILED DISCUSSION OF PREFERRED EMBODIMENTS

The composition of normal saliva of a human is:

| Constituent | Normal Range |
| --- | --- |
| Acidity (pH) | 6.4–7.0 |
| Titratable alkalinity (as 0.02 n HCl) | 90.0–100.0 ml per 100 ml. |
| Ammonia, as N | 2.0–10.0 mg per 100 ml. |
| Calcium, as Ca | 4.0–8.0 mg. per 100 ml. |
| Inorganic phosphate, as P | 10.0–25.0 mg. per 100 ml. |
| Chloride, as Cl | 30.0–60.0 mg. per 100 ml. |
| Carbonate, as $CO_2$ | 20.0–45.0 mg. per 100 ml. |
| protein | 200.0–400.0 mg. per 100 ml. |

Conditions in the mouth which predispose the fermentation of sugar with concomitant low pH, i.e., a pH of about 4.5, should be avoided. Saliva typically is not adequately buffered. Thus, repeated intake of diet with copious levels of fermentable sugars can lead to conditions of low pH which in turn leads to inhibition of desirable species such as Actinomyces and to proliferation of less desirable species as Streptomyces. This sets the stage for the development of caries.

The present invention provides a device for treating potable water, e.g. ordinary tap water, comprising a mixture or blend of an anion and a cation exchange resin or resins, a chelating agent, and a sparingly soluble calcium salt, all contained in a porous bag. As used herein, "ion exchange" is the reversible exchange of ions between a solid and a liquid in which the solid is not substantially changed. The solid typically is a 3-dimensional hydrocarbon network of styrene and divinyl benzene, plus a large number of ionizable groups. One set of ion exchange resins act as cation exchanger, and are strongly acidic. The cation exchange resins preferably are acidic and can exchange hydrogen ions for sodium ions, for example. The other set are anion exchange resins, typically quaternary ammonium types, can exchange chloride for sulfate, for example. A chelating agent such as hydroxycarboxylate, typically citric acid, and a sparingly soluble calcium salt, completes the mixture or blend and provides a buffering action. As used herein, a "sparingly soluble calcium salt" is a calcium salt having a solubility, in grams per 100 milliliters of water, of 0.2 to 0.25 at 38° C. The buffer acts between 5.5–6.0.

If desired, activated carbon optionally can be included. In a preferred embodiment of the invention, the anion and cation exchange resins, the chelating agent, the sparingly soluble calcium salt, and the optional activated carbon may be blended together, and packaged in a porous bag formed, e.g., of cotton, nylon, plastic or the like.

Typically, the cation ion exchange resin and anion exchange resins are present in a cation-to-anion exchange resin weight ratio of 2 to 1. The chelating agent typically is present in a weight ratio to the sum of the anion and cation exchange regions of 10 to 20%, preferably 12 to 14% based on the combined weight of anion and cation exchange resins. Preferred as a chelating agent is a bydroxycarboxylate, such as citric acid, although other food compatible chelating agents such as tartaric acid and succinic acid advantageously may be used in the present invention.

A sparingly soluble calcium salt such as monocalcium phosphate, is included as a minor component, typically 5 to 10 weight percent. Also optionally included is activated carbon. The activated carbon, if used, may comprise 30 to 50% of the mixture blend. Preferably, and so as to facilitate manufacture and avoid settling and separation of components, the activated carbon has a bulk density of about 23 lbs/ft$^3$, which matches, approximately, the density of the resin blend.

Typically, the several above described materials are blended together, and packaged in a flow-through bag similar to a tea bag. This permits the user to treat a single glass or pitcher of tap water. Alternatively, tap water may be treated, and bottled for future use.

The treated water may be used as a refreshing drink. The pH of the saliva in the mouth is shifted to about 5.5, so as to disfavor a growth of plaque.

Further features and advantages of the present invention will be seen from the following working examples which are given as illustrative only.

EXAMPLE 1

0.1 grams of Dowex Marathon C cation exchange resin in the hydrogen ion form, 0.05 grams of Dowex Marathon A anion exchange resin in the chloride ion form, 0.01 grams of citric acid, and 0.05 grams of monocalcium phosphate (MCP) are blended together. The blend was packaged in a porous, non-woven fabric bag, and used to treat a twelve ounce glass of tap water. The pH of the treated water had a pH of 5.5.

EXAMPLE 2

Example 1 was repeated with 0.3 grams of activated carbon, bulk density of about 23 lbs/ft$^3$ available from Norit Americas, Inc., added to the blend. Tap water was treated as before, and the tap water used as a mouthwash swish.

EXAMPLE 3

Example 1 was repeated, except that 0.5 grams of Dowex Marathon C and 0.25 grams of Dowex Marathon A, 0.06 grams of tartaric acid and 0.25 grams of MCP were used, except 0.06 grams of tartaric acid was employed in place of the citric acid. The resulting blend was used to treat a two liter pitcher of tap water for a few seconds or minutes.

It is to be understood that the examples described above are not meant to limit the scope of the present invention, but rather that the various changes may be made without departing from the spirit and scope thereof.

What is claimed is:

1. A device for treating potable water comprising a mixed buffer of a cation exchange resin in the hydrogen ion form and an anion exchange resin, a chelating agent and a sparingly soluble calcium salt, all contained in a porous, flow-through bag.

2. A device as claimed in claim 1, wherein the cation exchange resin and anion exchange resin are present in a weight ratio of about 2 to 1.

3. A device as claimed in claim 1, wherein the chelating agent is present in a weight ratio of about 10%.

4. A device as claimed in claim 1, wherein the sparingly soluble calcium salt is present in the range of 50 weight percent.

5. A device as claimed in claim 1, wherein the chelating agent comprises an hydroxycarboxylate.

6. A device as claimed in claim 1, wherein the chelating agent comprises citric acid.

7. A device as claimed in claim 1, wherein the chelating agent comprises tartaric acid.

8. A device as claimed in claim 1, wherein the chelating agent comprises succinic acid.

9. A device as claimed in claim 1, wherein the sparingly soluble calcium salt comprises monocalcium phosphate.

10. A device as claimed in claim 1, wherein the blend further includes activated carbon.

11. A device as claimed in claim 10, wherein the activated carbon is present in the amount of 50 volume percent of the blend.

12. A device as claimed in claim 10, wherein the activated carbon has an average bulk density of about 23 lbs/ft$^3$.

13. A device as claimed in claim 1, wherein the blend is packaged in a porous mesh for one-time use.

14. A device as claimed in claim 13, wherein the porous mesh comprises a porous bag formed of cotton, nylon or plastic.

15. A device as claimed in claim 1, wherein the cation ion exchange resin comprises an acidic compound.

16. A device as claimed in claim 1, wherein the anion ion exchange resin comprises a quaternary ammonium compound.

17. An oral rinse or beverage comprising potable water treated by contact with the device of claim 1.

18. A method of preventing build-up of dental plaque, which comprises rinsing the mouth with potable water previously treated by contact with the device of claim 1.

* * * * *